United States Patent [19]

Oshima et al.

[11] Patent Number: 5,059,530

[45] Date of Patent: * Oct. 22, 1991

[54] EXPRESSION VECTOR FOR HUMAN TNF

[75] Inventors: Takehiro Oshima; Shoji Tanaka; Shigekazu Matsukura, all of Osaka, Japan

[73] Assignee: Suntory Ltd., Osaka, Japan

[*] Notice: The portion of the term of this patent subsequent to Oct. 3, 2006 has been disclaimed.

[21] Appl. No.: 402,675

[22] Filed: Sep. 5, 1989

Related U.S. Application Data

[63] Continuation of Ser. No. 6,907,816, Sep. 16, 1986, Pat. No. 4,871,663.

[30] Foreign Application Priority Data

Sep. 30, 1985 [JP] Japan .................................. 60-217740

[51] Int. Cl.[5] .......................... C07H 15/12; C12P 2/02; B61K 37/02; C12N 1/20
[52] U.S. Cl. .................................. 435/69.5; 435/172.3; 435/320.1; 435/252.33; 935/11; 935/29; 935/31; 935/42; 935/56; 935/65; 536/27
[58] Field of Search .................... 435/69.1, 69.5, 172.3, 435/320, 252.33; 935/11, 29, 39, 42, 56, 65; 536/27

[56] References Cited

U.S. PATENT DOCUMENTS 4,871,663 10/1989 Ohshima et al. .................... 435/69.5

FOREIGN PATENT DOCUMENTS 0155549 9/1985 European Pat. Off. ............ 435/69.5
0158286 10/1985 European Pat. Off. ............ 435/69.5
03751 7/1986 PCT Int'l Appl. ................ 435/69.5

OTHER PUBLICATIONS

Platt, T. *Cell* vol. 24, pp. D-23, Apr. 1981, "Termination of Transcription and 180 Regulation of the Tryptophehopeonin *E Coli*".
Lacatena, et al., *Cell* vol. 37, pp. 1004–1014, Jul. 19 & 7, "Control of Initiation of pMB1 Replication: Purified Rop Protein and RNA I Affect Primer Formation in Vitro".
Nature, vol. 312, Dec. 20/27, 1984–D. Pennica et al., "Human Tumor Necrosis Factor: Precursor Structor, Expression and Homology to Lymphotoxin", pp. 724, 725.
Science, vol. 228, No. 4696, Apr. 12, 1985–A. M. Wang et al., "Molecular Cloning of the Complementary DNA For Human Tumor Necrosis Factor", pp. 149–154.

*Primary Examiner*—Robin L. Teskin
*Attorney, Agent, or Firm*—Cushman, Darby & Cushman

[57] ABSTRACT

The present invention provides a vector plasmid capable of efficient tumor necrosis factor (TNF) production, a process capable of efficient TNF production in a host transformed with said plasmid and a composition containing the TNF produced by said process.

The novel plasmid of the present invention is characterized by having inserted therein a DNA fragment that has a phage-derived promoter region upstream of a structural gene for TNF and in which a DNA fragment containing an *E. coli* gene-derived transcription termination coding base sequence (terminator) is joined immediately downstream of a base sequence coding for the termination of translation of said structural gene.

10 Claims, 6 Drawing Sheets

Fig. 1

10 — VAL-ARG-SER-SER-SER-ARG-THR-PRO-SER-ASP-LYS-PRO-VAL-ALA-HIS-VAL-VAL-ALA-ASN-PRO— 20

30 — GLN-ALA-GLU-GLY-GLN-LEU-GLN-TRP-LEU-ASN-ARG-ARG-ALA-ASN-ALA-LEU-LEU-ALA-ASN-GLY— 40

50 — VAL-GLU-LEU-ARG-ASP-ASN-GLN-LEU-VAL-VAL-PRO-SER-GLU-GLY-LEU-TYR-LEU-ILE-TYR-SER— 60

70 — GLN-VAL-LEU-PHE-LYS-GLY-GLN-GLY-CYS-PRO-SER-THR-HIS-VAL-LEU-LEU-THR-HIS-THR-ILE— 80

90 — SER-ARG-ILE-ALA-VAL-SER-TYR-GLN-THR-LYS-VAL-ASN-LEU-LEU-SER-ALA-ILE-LYS-SER-PRO— 100

110 — CYS-GLN-ARG-GLU-THR-PRO-GLU-GLY-ALA-GLU-ALA-LYS-PRO-TRP-TYR-GLU-PRO-ILE-TYR-LEU— 120

130 — GLY-GLY-VAL-PHE-GLN-LEU-GLU-LYS-GLY-ASP-ARG-LEU-SER-ALA-GLU-ILE-ASN-ARG-PRO-ASP— 140

150 — TYR-LEU-ASP-PHE-ALA-GLU-SER-GLY-GLN-VAL-TYR-PHE-GLY-ILE-ILE-ALA-LEU 157

Fig. 2

```
GTCAGATCATCTTCTCGAACCCCGAGTGACAAGCCTGTAGCCCATGTTGTAGCAAACCCT
ValArgSerSerArgThrProSerAspLysProValAlaHisValValAlaAsnPro
 +1                     10                        20

CAAGCTGAGGGCAGCTCCAGTGGCTGAACCGCGGGCCAATGCCCTCCTGGCCAATGGC
GlnAlaGluGlyGlnLeuGlnTrpLeuAsnArgArgAlaAlaAsnAlaLeuLeuAlaAsnGly
                30                        40

GTGGAGCTGAGAGATAACCAGCTGGTGGCCATCAGAGGGCCTGTACCTCATCTACTCC
ValGluLeuArgAspAsnGlnLeuValValProSerGluGlyLeuTyrLeuIleTyrSer
                50                        60

CAGGTCCTCTTCAAGGGCCAAGGCTGCCCCTCCACCCATGTCCTCACCCACCATC
GlnValLeuPheLysGlyGlnGlyCysProSerThrHisValLeuLeuThrHisThrIle
                70                        80

AGCCGCATCGCCGTCTCCTACCAGACCAAGGTCAACCTCCTCTCTGCCATCAAGAGCCCC
SerArgIleAlaValSerTyrGlnThrLysValAsnLeuLeuSerAlaIleLysSerPro
                90                        100

TGCCAGAGGGAGACCCCAGAGGGGCTGAGGCCAAGCCCTGGTATGAGCCCATCTATCTG
CysGlnArgGluThrProGluGlyAlaGluAlaLysProTrpTyrGluProIleTyrLeu
                110                       120

GGAGGGGTCTTCCAGCTGGAGAAGGGTGACCGACTCAGGCTGAGATCAATGGCCCGAC
GlyGlyValPheGlnLeuGluLysGlyAspArgLeuSerAlaGluIleAsnArgProAsp
                130                       140

TATCTCGACTTTGCCGAGTCTGGGCAGGTCTACTTTGGGATCATTGCCCTG
TyrLeuAspPheAlaGluSerGlyGlnValTyrPheGlyIleIleAlaLeu
                150          157
```

[VII]

↓ EcoRI/FILL-IN

↓ AhaIII

[VIII]

Fig. 6

EXPRESSION VECTOR FOR HUMAN TNF

This application is a continuation of Ser. No. 06/907,816 filed Sept. 16, 1986, now allowed U.S. Pat. No. 4,871,663.

BACKGROUND OF THE INVENTION

1. Field of the Invention

The present invention relates to a novel plasmid and use thereof. More particularly, the present invention relates to a plasmid capable of efficient expression of tumor necrosis factor (hereunder abbreviated as TNF) which is a protein having anti-tumor activity, a process for producing TNF using a host transformed with said plasmid, and a composition containing TNF produced by said process.

2. Prior Art

Figure 1:
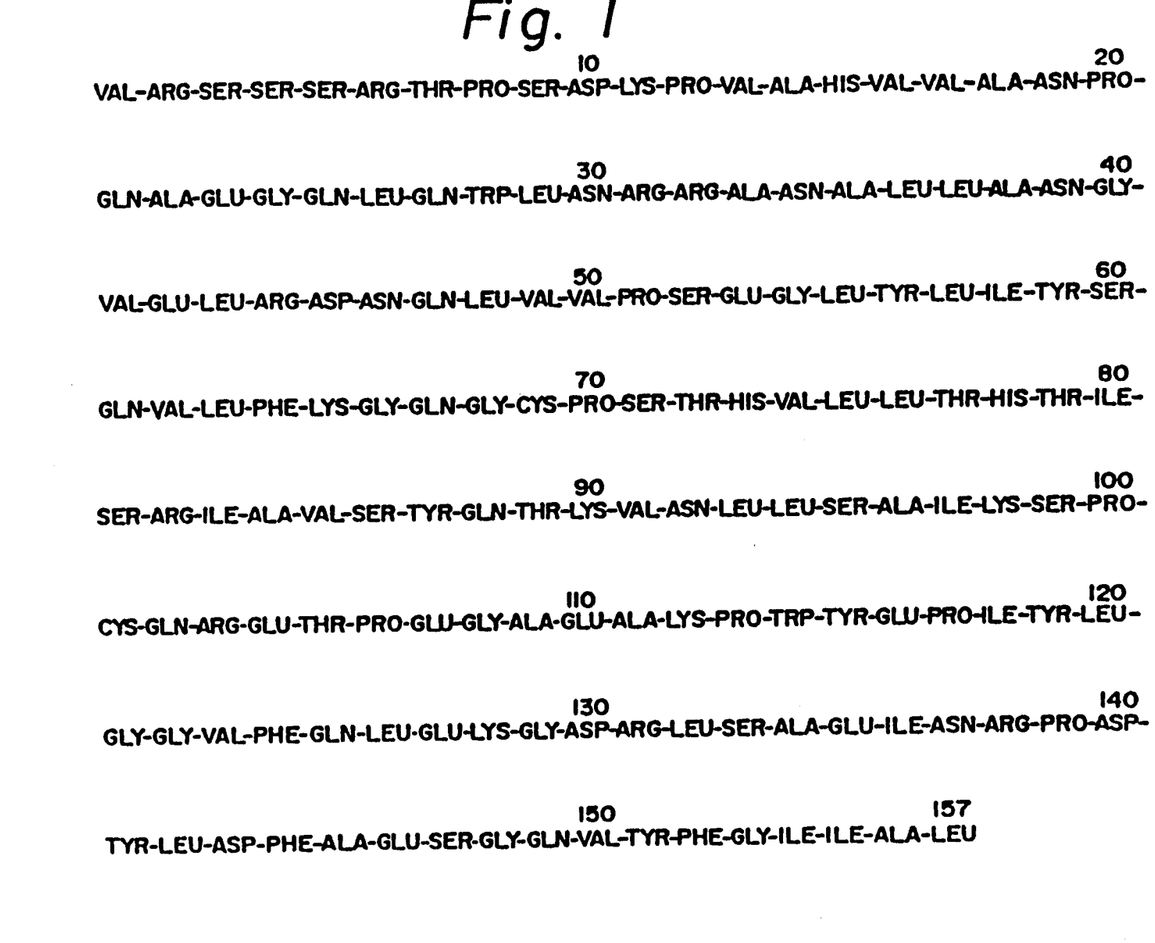
FIG. 1 is a diagram showing the amino acid sequence of TNF.
Figure 2:
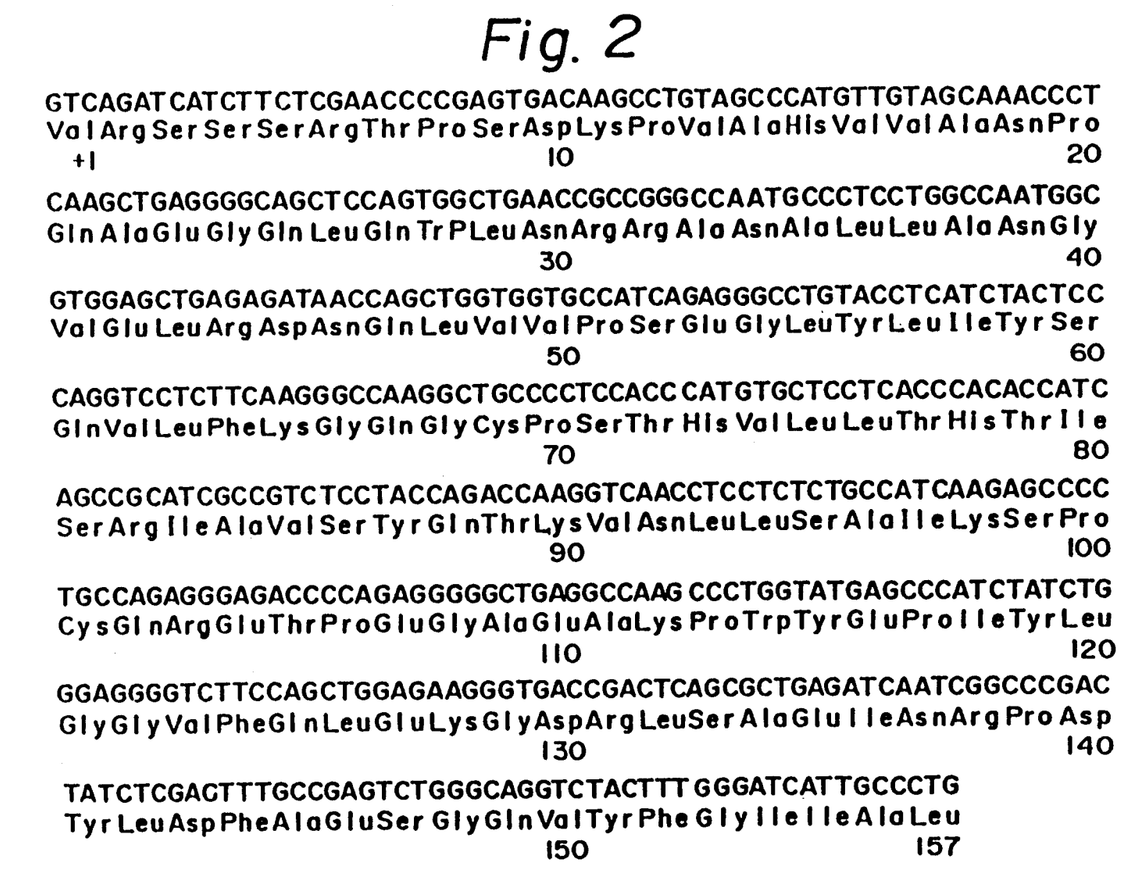
FIG. 2 is a diagram showing the TNF coding base sequence.

In 1975, Carswell and his co-workers found a substance having tumor cell killing or tumor necrotic activity in sera from animals previously sensitized with an immunopotentiator, and they referred to the substance as TNF (Proc. Natl. Acad. Sci. US 72: 3666-3670, 1975). It was later found that TNF caused hemorrhagic necrosis of various tumors with no apparent effect on the host and displayed cytocidal and cytostatic activities against several transformed cells (those which differentiated to tumors) in vitro without affecting normal cells. Because of these features, TNF holds great promise as an anti-tumor or cancer control agent. Ruff, H. R. & Gifford, G. E. reported in Lymphokines, vol. 2 (ed. Pick, E), 235-272, Academic Press, New York, 1981 that TNF was produced from activated macrophages in the organism. A substance having TNF activity was also isolated from the liquid culture of an established macrophage-like cell line. Most recently, two groups of researchers, with the aid of recombinant DNA techniques, revealed the amino acid sequence of human TNF (protein) produced by activated human macrophage-like cells (Pennica, D. et al.; Nature 312: 724-729, 1984; and Wang, A. M. et al.; Science 228: 149-154, 1985). In the study carried out by each group, mRNA of human TNF was isolated from activated human macrophage-like cells HL-60 and a cDNA library prepared from said mRNA was cloned for determination of the base sequence of TNF. At the same time, they purified TNF from the liquid culture of HL-60 and determined the amino terminal amino acids. As a result, they concluded that mature human TNF was a polypeptide composed of a 157-amino acid sequence starting with Val-Arg-Ser . . . and ending with Leu at the carboxyl terminus, as shown in FIG. 1, and that a TNF precursor was a protein wherein an additional polypeptide composed of 76 amino acids was attached to the amino terminal end of the 157-amino acid composed polypeptide. They also succeeded in producing said human TNF polypeptide in transformed E. coli. Pennica, D. et al. (ibid.) prepared a plasmid having said mature TNF gene inserted downstream from the E. coli tryptophan gene promoter, operator and ribosome-binding (Shine-Dalgarno: SD) sequence, and, using this plasmid as a vector, produced TNF in E. coli (W3110) displaying a cytocidal activity against L-929 of approximately $3 \times 10^5$ units per ml of culture at $A_{550}=1$, which corresponded to approximately $3 \times 10^5$ molecules of active TNF per cell (assuming a specific activity of $10^8$ units per mg of protein). Wang, A. M. et al (ibid.) prepared a ColE1 derived plasmid having mature TNF gene inserted downstream of the bacteriophage λPL promoter and the λ gene N ribosome binding sequence. This plasmid contained mutations conferring a temperature-sensitive Cop⁻ phenotype (Wang, E. M. et al., Proc. Natl. Acad. Sci. USA 79: 3570, 1982). The E. coli strain DG95 harboring this plasmid was cultured and extracts of induced cultured had $2.3 \times 10^5$ units of TNF activity per milliliter, with TNF protein representing about 8% of the total E. coli cellular protein (L-929 cells were used in TNF activity assay as in the study by Pennica et al. shown above).

SUMMARY OF THE INVENTION

As summarized above, mature human TNF composed of 157 amino acids can be produced using a plasmid incorporating the gene (cDNA) for the TNF and an E. coli or bacteriophage expression control associated gene. However, the productivity of these methods of producing mature human TNF is not necessarily high for commercial purposes and there exists a great need in the art for developing an expression system such as, for example, a novel expression vector capable of TNF production with higher efficiency.

One object, therefore, of the present invention is to provide a vector plasmid capable of efficient TNF production.

Another object of the present invention is to provide a process capable of efficient TNF production in a host transformed with that plasmid.

Still another object of the present invention is to provide a composition containing the TNF produced by said process.

DETAILED DESCRIPTION OF THE INVENTION

In order to attain the aforementioned objects, the present inventors made various studies of a vector capable of efficient production of mature human TNF in E. coli. As a result, the present inventors found that by using the novel plasmid specified below mature human TNF can be produced in E. coli with an efficiency that is much higher than that attained by the conventional methods. The novel plasmid is prepared by inserting into a pBR322-derived plasmid, which may, as required, be depleted of part of a plasmid DNA replication controlling gene region (repressor of primer, which is hereinafter abbreviated as rop), a DNA fragment that has, upstream of a structural TNF gene, a region that contains one or more promoter regions derived from a T4 phage DNA fragment and which is accompanied by the lambda phage or T4 phage gene (T4 gene 32)-derived ribosome binding sequence (also known as the Shine-Dalgarno sequence); said DNA fragment also has an E. coli-gene derived, transcription termination coding base sequence (terminator) attached immediately downstream of a base sequence coding for the termination of translation of said structural gene.

The novel plasmid of the present invention is characterized by having inserted therein a DNA fragment that has a phage gene-derived promoter region upstream of a structural gene for TNF and in which a DNA fragment containing an E. coli gene-derived transcription termination coding base sequence (terminator) is joined immediately downstream of a base sequence coding for the termination of translation of said structural gene.

The TNF expression vector plasmid of the present invention may be obtained by modifying, in the manners described hereinafter, pBR322-PL-T4-hTNF, or the plasmid into which a gene coding for the amino acid sequence shown in FIG. 1 has been integrated in an expressible manner (the E. coli strain C600 into which this plasmid has been introduced has been deposited with the Culture Collection of the Deutsche Sammlung von Mikroorgamismen, Göttingen, West Germany, under Accession Number DSM3175; this plasmid was distributed to the inventors by courtesy of Biogen S. A., Switzerland). The plasmid pBR322-PL-T4-hTNF has inserted therein a DNA fragment that has been so constructed that the TNF gene can be expressed under the regulatory control of the lambda phage PL promoter and the T4 phage fragment derived T4 promoter represented by T4 gene32. The plasmid also uses the T4 phage-derived ribosome binding sequence (SD sequence). The accompanying FIG. 3(I) shows the restriction enzyme map of the plasmid pBR322-PL-T4-hTNF.

Figure 3:
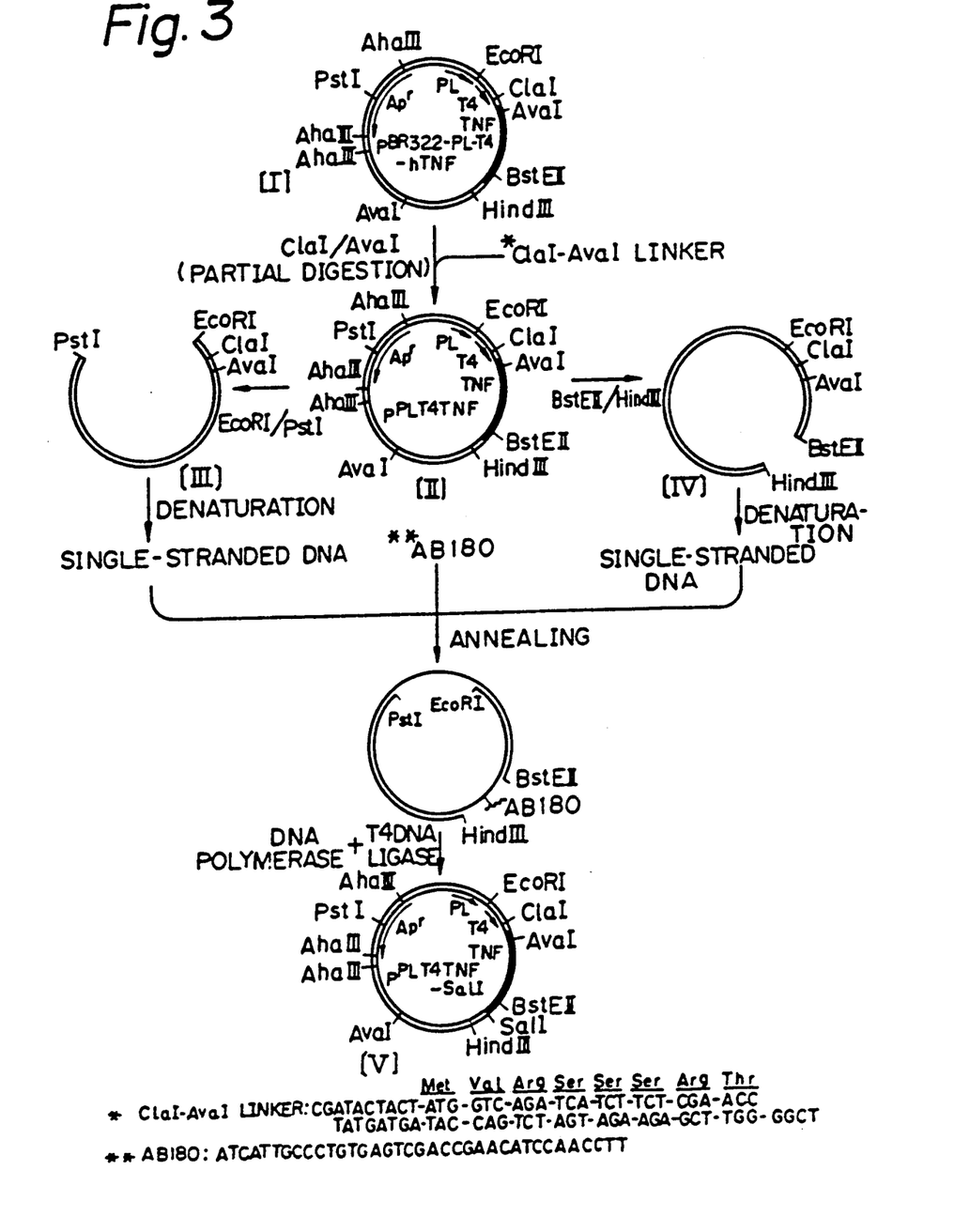
FIG. 3 is a diagram showing the procedures for constructing the plasmid pPLT4TNF-SalI.

First, a small ClaI-AvaI DNA fragment on pBR322-PLT-4-hTNF that contains the DNA encoding part of the amino terminus of the TNF peptide and part of the DNA upstream of the 5' end of the translation initiation site is replaced by a chemically synthesized ClaI-AvaI linker represented by the following base sequence:

```
  CGATACTACTATGGTCAGATCATCTTCTCGAACC
    TATGATGATACCAGTCTAGTAGAAGAGCTTGGGGCT
  (ClaI)                               (AvaI)
``` thereby obtaining the plasmid pPLT4TNF [FIG. 3(II)]. This step is performed in order to convert the base sequence on pBR322-PL-T4-hTNF that codes for the amino terminal amino acid of TNF peptide into the base sequence of the TNF cDNA identified in Pennica, D. et al. and Wang, A. M. et al. (ibid.) since the corresponding region on pBR322-PL-T4-hTNF differs slightly from the base sequence of said cDNA.

Subsequently, in order to enable the E. coli-derived terminator to be readily joined immediately downstream of the codon for terminating the translation of the TNF structural gene, the plasmid pPLT4TNF-SalI having a SalI cleavage site immediately downstream of said translational termination codon is constructed in accordance with the in vitro mutation method described in Morinaga, Y. et al., Biotechnology, 2: 636–639, 1984 (see FIG. 3). The SalI cleavage site may be inserted by another version of the in vitro mutation method using the M13 phage as described in Zoller, H. J. & Smith, M., Nucl. Acid. Res., 10: 6487, 1982, and in Japanese Patent Application No. 241457/1983.

Figure 4:
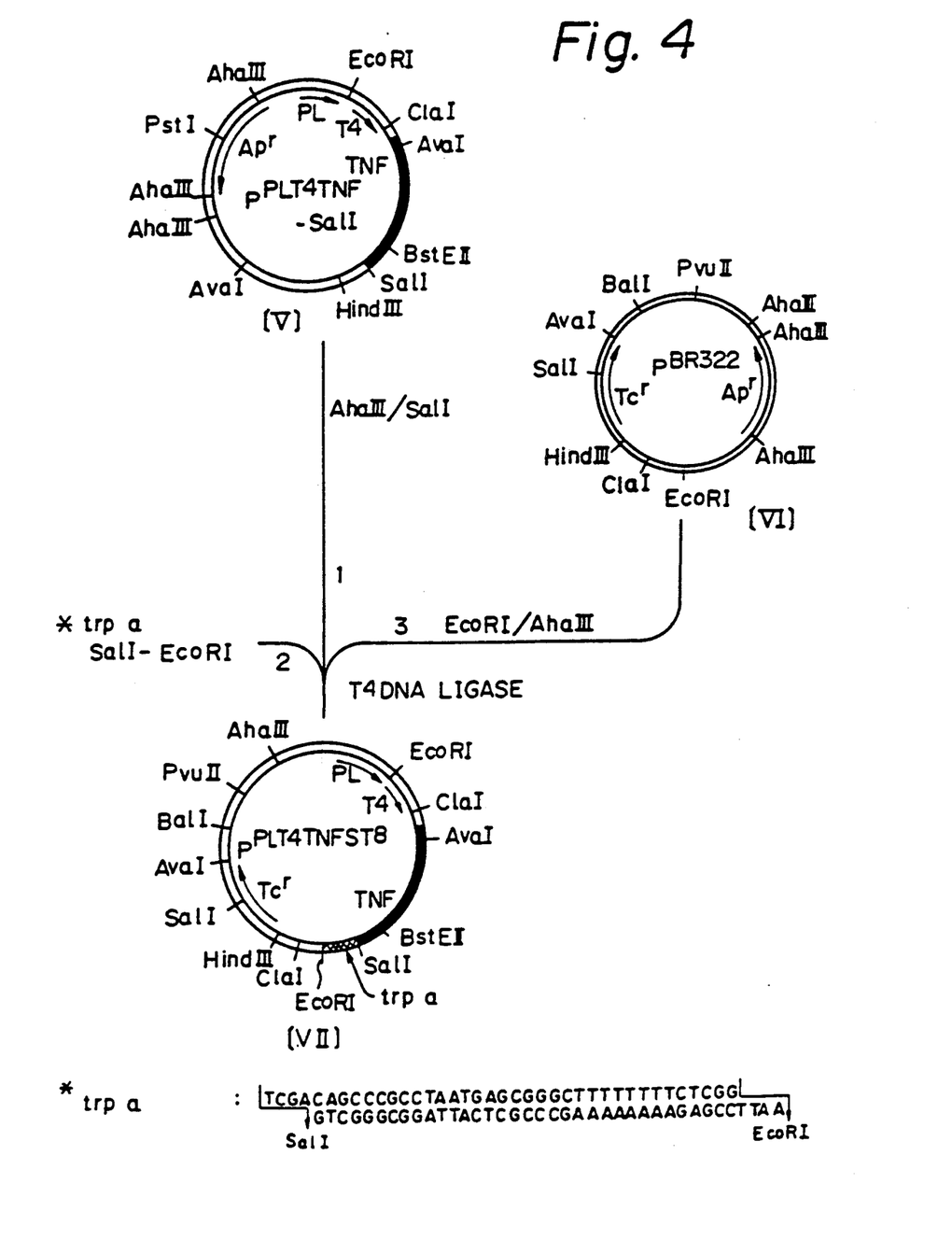
FIG. 4 is a diagram showing the procedures for constructing the plasmid pPLT4TNFST8.

The plasmid pPLT4TNF-SalI has the restriction enzyme map shown in FIG. 4(V) and is cleaved with AhaIII and SalI to obtain a fragment (1) having the PLT4 promoter and the TNF gene. Using a T4DNA ligase, the fragment (1) is ligated with a chemically synthesized DNA segment (2) and an EcoRI-AhaIII DNA fragment (3) in a three-fragment ligation. Segment (2) ends with a SalI cohesive site and an EcoRI cohesive site and has the following base sequence (terminator trp a:trp a):

```
TCGACAGCCCGCCTAATGAGCGGGCTTTTTTTCTCGG
    GTCGGGCGGATTACTCGCCCGAAAAAAAAGAGCCTTAA
  SalI                                        EcoRI
```

Fragment (3) is a large (3.2 kb) fragment that contains a tetracycline resistance gene Tc$^r$ and which is obtained by cleaving the plasmid pBR322 with AhaIII and EcoRI. By this ligation is obtained the plasmid pPLT4TNFST8 that has the E. coli gene-derived terminator inserted immediately downstream of the TNF structural gene and which has the tetracycline resistance gene Tc$^r$ [the restriction map of this plasmid is shown in FIG. 4(VII)]. The construction of this plasmid can be readily verified by screening the transformants for tetracycline resistence and ampicillin sensitivity.

The plasmid pPLT4TNFST8 is introduced, for transformation purposes, into a plasmid such as pCI$_{857}$ that is capable of expressing the lambda phage temperature-sensitive repressor gene (e.g. cI$_{857}$) and which is compatible with a plasmid like pBR322. For details of the plasmid pCI$_{857}$ (hereunder abbreviated as CI) that harbors the kanamycin resistance gene and the lambda phage temperature-sensitive repressor gene, cI$_{857}$, see Gene 22, 103-113, 1983 (Remant, E., Tsao, H. & Fiers, W.) The host E. coli to be transformed by the plasmid that is so constructed as to permit expression of an exogenous gene under the regulatory control of the lambda phage PL promoter is preferably the one having the pCI$_{857}$ (CI) plasmid or a lambda phage lysogenized E. coli that has said temperature-sensitive repressor gene on the chromosome. A particularly preferred E. coli strain is CI plasmid containing WA802/CI or W3110/CI.

The E. coli transformed with pPLT4TNFST8 produces a very high yield of human TNF (up to $1.9 \times 10^7$ units per milliliter) as compared with the value attained by conventional techniques. In order to render this plasmid easier to handle and more productive, the promoter region in the plasmid is converted as shown in FIG. 5 (conversion from the chain of PL and T4 promoters to a single T4 promoter: pPLT4TNFST8→pT4TNFST8) or, alternatively, the plasmid pT4TNFST8rop$^{31}$ is constructed, this being deficient of the rop (repressor of primer) gene which serves to control the replication of the pBR322-derived plasmid DNA.

Conversion from the PLT4 promoter to the T4 promoter is performed in order to broaden the spectrum of hosts that can be transformed with the plasmid (the host that can be used in expressing an exogenous gene under the control of the T4 promoter is not limited to the *E. coli* strain harboring a lambda phage temperature-sensitive repressor gene like cI$_{857}$ as in the case of expression under the control of the PLT4 promoter); elimination of the function of the rop gene is carried out in order to ensure more efficient plasmid replication within the host cell.

The *E. coli* strain that has been transformed by one of the plasmids constructed by the procedures described above is shake cultured or cultured under aeration and agitation in a suitable medium, and the TNF production can be determined by SDS polyacrylamide gel electrophoresis (hereunder abbreviated as SDS PAGE) and TNF activity assaying. As will be shown specifically in the Examples that follow, TNF activity assaying may be done in accordance with the method described in Lymphokines, vol. 2, 235, 1981, Academic Press.

Figure 5:
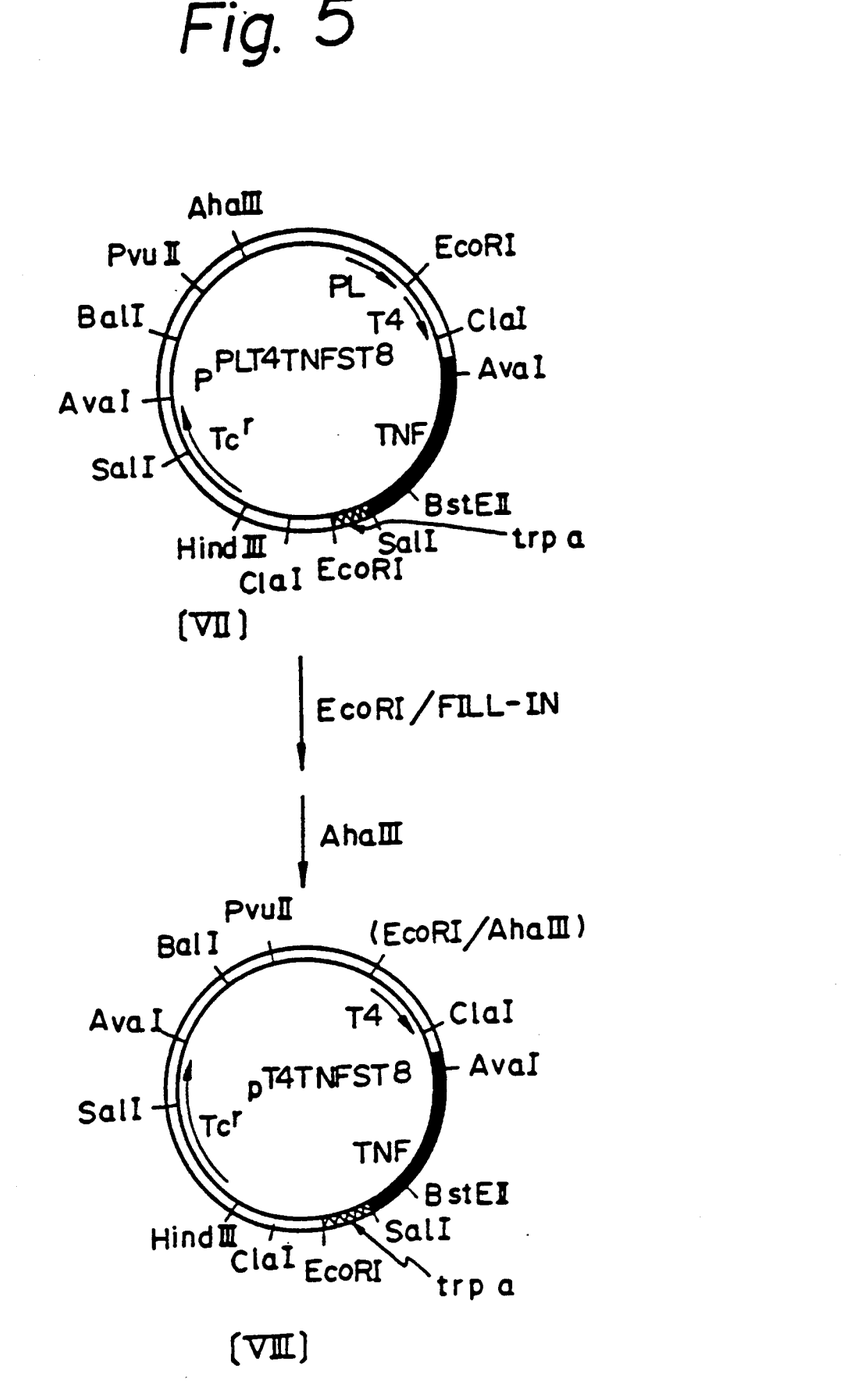
FIG. 5 is a diagram showing the procedures for constructing the plasmid pT4TNFST8.
Figure 6:
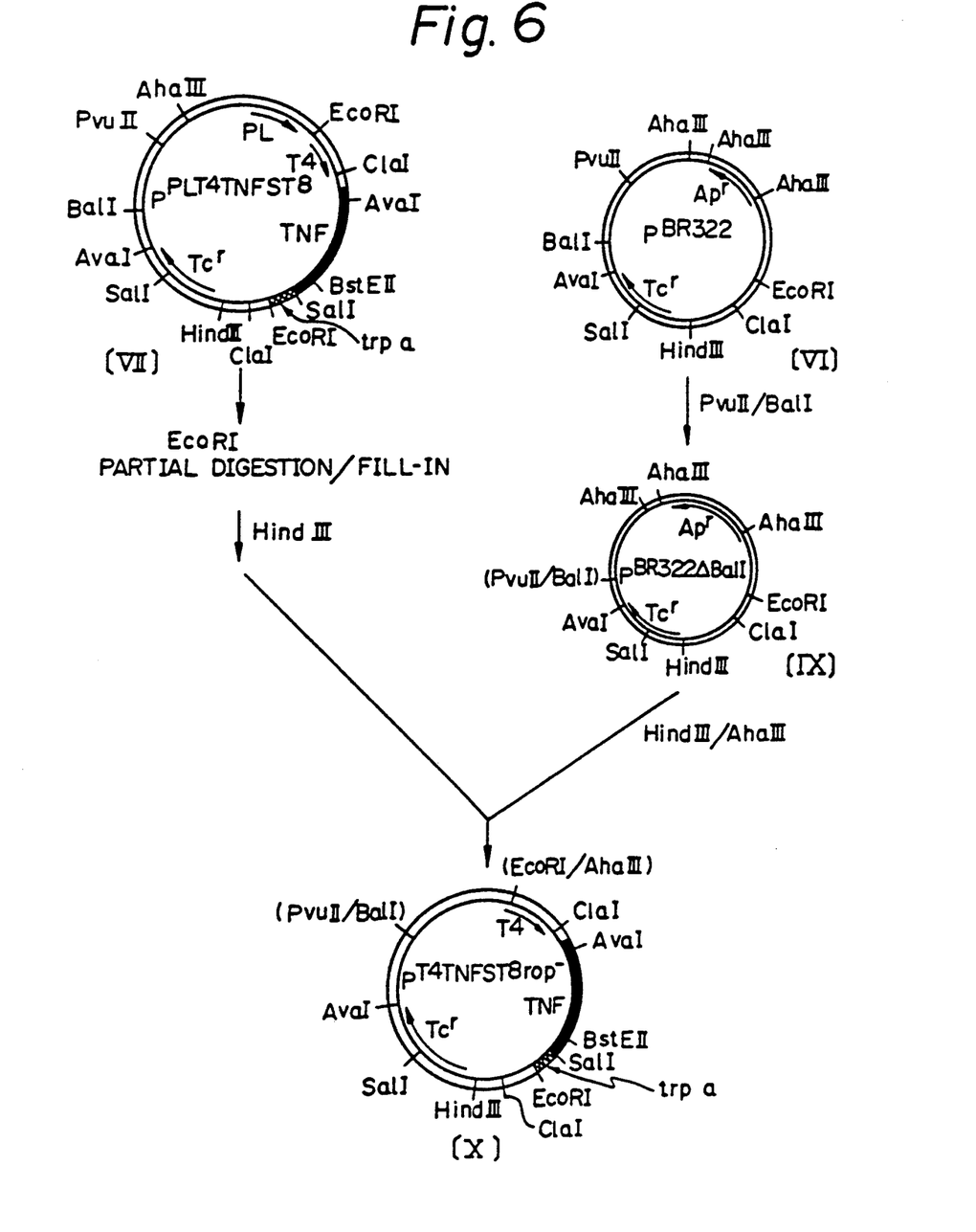
FIG. 6 is a diagram showing the procedures for constructing the plasmid pT4TNFST8rop⁻.

The *E. coli* strain W3110 transformed with the plasmids constructed by the procedures shown in FIGS. 5 and 6 attains high levels of TNF productivity. Especially, *E. coli* W3110/pT4TNFST8rop$^-$ obtained by transformation with the plasmid pT4TNFST8rop$^-$ constructed by the procedures shown in FIG. 6 achieves surprisingly high yields of TNF ($2.8 \times 10^7$–$1.9 \times 10^8$ units per milliliter) after cultivation in a jar fermenter. The TNF protein accumulation as estimated by SDS-PAGE represents no less than 40% of the total cellular protein of the transformed *E. coli*. The transformant WA802/pT4TNFST8rop$^-$ obtained by introducing the plasmid pT4TNFST8rop$^-$ into another *E. coli* strain WA802 also achieves high TNF yields ranging from $3.0 \times 10^7$ to $6.7 \times 10^7$ units per milliliter.

There is no prior art plasmid that is known to be capable of attaining such high levels of TNF production. For example, the plasmid reported by Wang, A. M. et al. in Science 228, 149–154, 1985 attained only about $3 \times 10^5$ units of TNF activity per milliliter as detected by the same assay method. The activity displayed by the pBR322-PL-T4-hTNF from which the plasmid of the present invention is constructed is approximately $5$–$6 \times 10^5$ units per milliliter. It is therefore clear that the plasmids of the present invention, especially pPLT4TNFST8 and pT4TNFST8rop$^-$, offer remarkable advantages that have not been obtained by the prior art techniques of TNF production.

The *E. coli* strains W3110/pT4TNFST8 and WA802/pT4TNFST8 that are obtained by transformation with the plasmid pT4TNFST8 constructed by the procedures shown in FIG. 5 are somewhat inferior to the *E. coli* strains transformed by pPLT4TNFST8 in terms of TNF productivity (approximately $5 \times 10^6$ units per ml for each strain), but as already mentioned, "unexpected advantages" for TNF production can be attained by depleting the plasmid pT4TNFST8 of the functional rop gene.

The TNF produced by *E. coli* that has been transformed with the plasmid of the present invention may be extracted by suitable procedures and purified to a pharmaceutically acceptable level by appropriate techniques such as DEAE-Sepharose column chromatography, dye adsorption affinity column chromatography, and gel filtration.

The following examples are provided for the purpose of further illustrating the present invention but are by no means intended as limiting.

The TNF gene used in the examples was a cDNA fragment prepared from the mRNA produced by activated human macrophage-like cells, but this may be replaced by any chemically synthesized DNA that is capable of encoding the amino acid sequence shown in FIG. 1. The *E. coli* phage gene-derived promoter and SD sequence may be replaced by other types of promoter and SD sequence depending upon the host cell used, such as, for example, those which derive from *E. coli* trp gene and lpp gene, as well as modifications of such promoter and SD sequence. The host *E. coli* strain WA802 and W3110 may also be replaced by other *E. coli* strains, depending upon the plasmid used.

EXAMPLES

The basic procedures for recombinant DNA technology, such as the cleavage of plasmid DNA with restriction enzymes, ligation of DNA fragments, transformation of *E. coli*, screening of the transformants, and isolation of plasmid or fragments, were followed in accordance with the methods described in Maniatis, I. et al., Molecular Cloning—A Laboratory Manual, Cold Spring Harbor Laboratory, 1982, and Radriquez, R. L. and Tait, R. C., Recombinant DNA Techniques—An Introduction, Addison-Wesley Publishing Company, 1983.

EXAMPLE 1

Construction of plasmids pPLT4TNF and pPLT4TNF-SalI

Five micrograms of plasmid pBR322-PL-T4-hTNF [the *E. coli* strain C600/CI transformed with this plasmid has been deposited with the Culture Collection of the Deutsche Sammlung von Mikroorganismen, Göttingen, West Germany, under Accession Number DSM3175, and the restriction enzyme map of this plasmid is shown in FIG. 3(I)] was completely digested with the restriction enzyme ClaI and digested partially with AvaI (0.5 unit). Half a microgram of a chemically synthesized ClaI-AvaI linker DNA fragment having the base sequence:

```
CGATACTACTATGGTCAGATCATCTTCTCGAACC
    TATGATGATACCAGTCTAGTAGAAGAGCTTGGGGCT
(ClaI)                                  (AvaI)
``` was mixed in a ligation buffer and ligated with the previously obtained DNA fragment using 2 units of a T4DNA ligase. The solution was used to transform the *E. coli* strain W3110/CI (deposited at the ATCC, Rockville, Md., under accession number 27325), and from the transformants that were ampicillin-resistant and had the TNF producing capability, the desired plasmid pPLT4TNF [indicated in FIG. 3(II)] was isolated by routine procedures.

Subsequently, a SalI cleavage site was inserted at a point immediately downstream of the TNF structural gene on the plasmid pPLT4TNF in accordance with the method of Morinaga, Y. et al. described in Biotechnology 2: 636–639, 1984. First, the pPLT4TNF was divided into two portions. One of them was completely cleaved with EcoRI and PstI to obtain a double-stranded DNA fragment that was deficient of the PL promoter containing DNA fragment as shown in FIG.

3(III). The other portion was cleaved with HindIII and BstEII to obtain a double-stranded DNA fragment that was deficient of a fragment containing part of the TNF gene at its 3' end as shown in FIG. 3(IV). The two DNA fragments (III) and (IV) were mixed with AB180 that was a chemically synthesized single-stranded DNA having a SalI cleavage site and the base sequence: 5'-ATCATTGCCCTGTGAGTCGACCGAACATC-CAACCTT-3'. By heating at 100° C., the double-stranded DNA was changed to single-stranded DNA, which then was slowly cooled to form a double-stranded chain by annealing. To the reaction solution, dNTPs and DNA polymerase (Klenow fragment), as well as T4DNA ligase and ATP were added and reaction was carried out to form a closed circular double-stranded DNA. The resulting solution was used to transform the E. coli strain W3110/CI and ampicillin-resistant transformants were selected. Plasmid was isolated from the transformants and restriction enzyme analysis revealed that it was the desired plasmid pPLT4TNF-SalI which, as shown in FIG. 3(V), contained a SalI cleavage site immediately downstream of the TNF structural gene.

EXAMPLE 2

Construction of plasmid pPLT4TNFST8

The plasmid pPLT4TNF-SalI constructed in Example 1 was subjected to the following procedures (see FIG. 4) in order to construct the plasmid pPLT4TNFST8 wherein the terminator trp a was inserted at a point immediately downstream of the codon for terminating the translation of the TNF structural gene on pPLT4TNF-SalI and whose drug resistance marker was tetracycline, rather than ampicillin.

A fragment (1) was obtained by cleaving pPLT4TNF-SalI with AhaIII and SalI and which harbored the PLT4 promoter and the TNF gene. Using a T4DNA ligase, this fragment was ligated with a chemically synthesized DNA segment (2) and an EcoRI-AhaIII DNA fragment (3) in a three-fragment ligation. Segment (2) ended with a SalI cohesive site and an EcoRI cohesive site and had the following base sequence (terminator trp a:trp a):

```
TCGACAGCCCGCCTAATGAGCGGGCTTTTTTTCTCGG
    GTCGGGCGGATTACTCGCCCGAAAAAAAAGAGCCTTAA
SalI                                         EcoRI.
```

Fragment (3) was a large (3.2 kb) fragment that contained the tetracycline resistance gene Tc$^r$ and which was obtained by cleaving the plasmid pBR322 [for its restriction enzyme map, see FIG. 4(VI)] with AhaIII and EcoRI. The ligation product was used to transform the E. coli strains W3110/CI and WA802/CI (described by Wood in J. Mol. Biol. 16:118 (1966); available from E. coli Genetic Center, Dept. of Human Genetics, Yale University School of Medicine, 333 Cedar St., New Haven, Conn. 06510, U.S.A.). The transformants were tetracycline-resistant and screened for ampicillin sensitivity. Plasmid was isolated from each of the transformants by routine procedures and restriction enzyme analysis verified the construction of the desired plasmid pPLT4TNFST8 having the restriction enzyme map shown in FIG. 4(VII).

The E. coli strain WA802/CI/pPLT4TNFST8 obtained by transformation with the plasmid pPLT4TNFST8 was named SBM 281 and has been deposited with the Fermentation Research Institute, the Agency of Industrial Science and Technology, under Deposit Number FERM BP-906.

EXAMPLE 3

Construction of plasmid pT4TNFST8

Five micrograms of the plasmid pPLT4TNFST8 obtained in Example 2 was partially digested with EcoRI (0.5 unit) and the EcoRI cohesive end was made blunt (filled in) with a DNA polymerase in the presence of dNTPs (i.e., dATP, dGTP, dTTP and dCTP). Subsequently, the pPLT4TNFST8 was cleaved at the AhaIII site by addition of 5 units of AhaIII and ligation was conducted with a T4DNA ligase. The resulting ligation solution was used to transform the E. coli strains WA802 and W3110. Plasmid DNA was isolated from the tetracycline-resistant transformants (which were named WA802/pT4TNFST8 and W3110/pT4TNFST8) and restriction enzyme analysis revealed that these transformants had the desired plasmid pT4TNFST8 [as represented by the restriction enzyme map shown in FIG. 5(VIII)].

EXAMPLE 4

Construction of plasmid pT4TNFST8rop$^-$

The plasmid pT4TNFST8rop$^-$ which lacked the pBR322-derived rop (repressor of primer) gene on pPLT4TNFST8 having the function of controlling plasmid DNA replication was constructed by the following procedures.

Plasmid pBR322 having the restriction enzyme map shown in FIG. 6(VI) was cleaved with PvuII and BalI (each providing a blunt end), ligated with a T4DNA ligase and used to transform the E. coli strain WA802. The transformants were screened for resistance to both ampicillin and tetracycline, and from the active transformants the plasmid pBR322ΔBalI lacking the small PvuII-BalI DNA fragment on pBR322 as shown by the restriction enzyme map in FIG. 6(IX) was isolated.

The plasmid pBR322ΔBalI was cleaved with HindIII and AhaIII. The plasmid pPLT4TNFST8 that was obtained in Example 2 and which had the restriction enzyme map shown in FIG. 6(VII) was partially digested with EcoRI, filled in at the EcoRI cohesive end (see Example 3) and cleaved with HindIII. The two DNA fragments were ligated with a T4DNA ligase. The ligation product was used to transform the E. coli strains WA802 and W3110 and the transformants were screened for tetracycline-resistant clones. Plasmid DNA was isolated from the clones and restriction enzyme analysis verified the construction of the desired plasmid pT4TNFST8rop$^-$ having the restriction enzyme map shown in FIG. 6(X). The E. coli strains WA802 and W3110 having the plasmid pT4TNFST8rop$^-$ were named WA802/pT4TNFST8rop$^-$ and W3110/pT4TNFST8rop$^-$, respectively, and their capability of TNF production was determined.

EXAMPLE 5

Assaying the TNF activity of transformants

The transformants were cultured for 15 hours at 37° C. in an LB medium (0.5% yeast extract, 1% Bacto-tryptone, 0.5% NaCl, pH 7.0) containing 10 μg/ml of tetracycline (plus 40 μg/ml of kanamycin for the transformants having the CI plasmid). The liquid culture (0.5 ml) was centrifuged and the resulting cell pellet was suspended in 0.5 ml of a PBS solution (Nissui Seiyaku Co., Ltd.) containing 250 μg/ml of lysozyme (Gradel, albumen lysozyme of Sigma) and reacted at 0° C. for 30 minutes. Lysis was completed by repeating three cycles of freezing in ethanol/dry ice and thawing at 37° C. The resulting lyzed solution was centrifuged at 12,000 rpm for 5 minutes and the supernatant was used as a sample for TNF activity assaying that was determined by a slightly modified version of the method described by Ruff, M. R. and Gifford, E. G., Lymphokines, (ed. by Pick, E.), vol. 2, 235-272, Academic Press, New York (1981).

One tenth of a milliliter of cell suspension in Eagle's MEM plus 10% fetal bovine serum, 0.1% $NaHCO_3$ and 0.03% glutamine ($6\times10^5$ L-929 cells in log growth stage per ml which were deposited at ATCC under Accession Number CCL-1 and which were subspecies of mouse L cells) was added to each of the 96 wells in a flat bottom tissue culture microplate (Nunc) for 0.1 ml of the supernatant sample that had been serially diluted in the same Eagle's MEM. To each well, Actinomycin D (Makor Chemicals) had been added to a final concentration of 1 μg/ml. The microplate was incubated at 37° C. for ca. 18 hours in air containing 5% $CO_2$. After incubation, the supernatant was discarded and 0.1 ml of a 0.5% aqueous Crystal Violet solution containing 20% methanol was added to each well, so as to stain adherent L-929 cells for 15 minutes at room temperature. The stained microplate was thoroughly washed with water. After drying, 0.1 ml of 33% aqueous acetic acid solution was added to extract the dye from the stained cell lysate. The absorbance of the extract at 577 nm was measured with Titertek Multiskan Spectrophotometer. The reciprocal of the dilution for the sample having an absorption corresponding to 50% of the value for the control was used as the TNF activity of the sample and indicated in units/ml (U/ml). At least four measurements were made for each sample and their average was taken.

The TNF activities of the transformants obtained by transformation with the plasmids prepared in accordance with the present invention were determined by the procedures described above and compared with the values for the transformants obtained by transformation with the original TNF producing plasmid, pBR322-PL-T4-hTNF.

The E. coli strains WA802/CI and W3110/CI transformed by the original TNF producing plasmid pBR322-PL-T4-hTNF had TNF activity levels in the range of approximately $5-6\times10^5$ U/ml.

The transformants WA802/CI/pPLT4TNFST8 and W3110/CI/pPLT4TNFST8 prepared in Example 2 both exhibited a maximum TNF activity of $1.9\times10^7$ U/ml, which was over 30 times the activity level for the original plasmid. The transformants WA802/pT4TNFST8 and W3110/pT4TNFST8 obtained in Example 3 by transformation with the plasmid harboring the T4 promoter rather than the PLT4 promoter had a slightly lower TNF activity level ($5.4\times10^6$ U/ml). However, the transformants WA802/pT4TNFST8rop$^-$ and W3110/pT4TNFST8rop$^-$ obtained in Example 4 by transformation with the plasmid pT4TNFST8rop$^-$ lacking the rop gene on pT4TNFST8 had very high levels of TNF activity. The transformant W3110/pT4TNFST8rop$^-$ exhibited particularly high levels of TNF production ($2.8\times10^7$-$1.9\times10^8$ U/ml) after cultivation in a jar fermenter; SDS PAGE analysis showed that the TNF protein represented no less than 40% of the total cellular protein in the transformant. These activity levels ranged from 40 up to 300 times the value for the original plasmid ($5-6\times10^5$ U/ml). The transformant WA802/pT4TNFST8rop$^-$ also exhibited a high TNF yield ($3.0-6.7\times10^7$ U/ml).

EXAMPLE 6

TNF purification

The transformant W3110/pT4TNFST8rop$^-$ was cultured in a 3-liter jar fermenter (net capacity, 2 liters) at 37° C. for 15 hours in a GC medium (2% glycerin, 3% casamino acids, 0.5% $KH_2PO_4$, 0.2% yeast extract, 0.1% $MgSO_4.7H_2O$, pH 6.5) containing 10 μg/ml of tetracycline. The culture was centrifuged and the cell pellet was suspended in a 10 mM Tris-HCl buffer (pH 8, hereunder simply referred to as Tris buffer). The suspension was disrupted with a high-pressure homogenizer (Manton-Gaulin Laboratory Homogenizer 15M-8TA) at 8,000 psi, and centrifuged. To the supernatant, ammonium sulfate was added to an 80% saturation and the mixture was centrifuged to precipitate the protein. The protein was dissolved in a Tris-buffer, and after thorough dialysis against the same buffer, was subjected to anion exchange chromatography on a carrier, "DEAE Toyopearl 650C" (Toyo Soda Manufacturing Co., Ltd.) The TNF active fractions were eluted by passage of a sodium chloride solution having a linear density gradient of 0-300 mM. The TNF active fractions were diluted with a Tris-buffer (pH 7) and loaded onto a column of DEAE Sepharose CL-6B (Pharmacia). The TNF active fractions were recovered by passage of a sodium chloride solution having a linear density gradient of 0-200 mM.

SDS analysis showed that the resulting TNF active fractions were sufficiently pure to provide a substantially single protein band having the TNF activity. In order to further increase their purity, the fractions were loaded onto a column of Matrex Blue A (Amicon Co.) and a column of Phenyl Sepharose CL-4B (Pharmacia), The TNF sample obtained by these chromatographic procedures could be further purified by gel filtration using Sephacryl S200 as a carrier.

The finally obtained TNF sample was purified by a reversed-phase high performance liquid chromatographic apparatus (Shimazu Corporation) using a Microbonder Pack $C_{18}$ column (Waters Instruments, Inc.), an the amino acid composition of the sample was analyzed by routine procedures using an automatic amino acid analyzer (Hitachi, Ltd.) The detected amino acid composition was in close agreement with what was predicted from the amino acid sequence shown in FIG. 1. It was estimated that the purified protein had about 7% of the methionine residue attached to the amino terminus.

The amino terminal amino acid sequence of the purified protein was analyzed by the Edman method with a gasphase protein sequencer Model 470A (Applied Biosystems). The result was in complete agreement with the amino acid sequence shown in FIG. 1.

While TNF production by W3110/pT4TNFST8rop$^-$ has been described in the foregoing pages, it should be noted that a substantially pure TNF protein could be obtained from the other TNF producing transformants prepared in accordance with the present invention when they were treated by the same procedures described above.

The TNF thus obtained is sufficiently pure to be used as a medicine and, hence, can be incorporated as the effective ingredient of a TNF containing pharmaceutical composition.

Advantages of the Invention

As described in detail hereinbefore, the transformants obtained by transformation with the novel plasmids prepared in accordance with the present invention are capable of very efficient TNF production. The TNF activity levels achieved by these transformants are within the range of approximately 40–300 times the value attained by the prior art transformant, and the TNF protein produced represents no less than 40% of the total cellular protein in the transformants. This suggests the great commercial value of the present invention in that it is capable of large-scale preparation of TNF having a pharmaceutically acceptable high level of purity.

We claim:

1. A plasmid capable of efficient expression of human tumor necrosis factor (TNF) in *Escherichia coli* (*E. coli*), said plasmid comprising a structural gene for human TNF, a promoter element selected from the group consisting of the T4 phage promoter and a hybrid PL-T4 phage promoter, and a DNA fragment which comprises the trpA terminator, said promoter being operably linked to the hTNF structural gene, and said DNA fragment which comprises the trpA terminator being located at a point immediately downstream of said structural gene.

2. A plasmid according to claim 2 which is of the ColE1 type and which lacks a pBR322-derived rop (repressor of primer) gene, said gene having a function of controlling the replication of said plasmid.

3. A plasmid according to claim 1 wherein a coding sequence for said terminator is contained in the following DNA fragment:

TCGACAGCCCGCCTAATGAGCGGGCTTTTTTTTCTCGG
    GTCGGGCGGATTACTCGCCCGAAAAAAAAGAGCCTTAA.

4. A plasmid according to claim 1 wherein said human TNF is a protein comprising the following amino acid sequence (I):

(I)
1
VAL—ARG—SER—SER—SER—ARG—THR—PRO—

10
SER—ASP—LYS—PRO—VAL—ALA—HIS—VAL—

20
VAL—ALA—ASN—PRO—GLN—ALA—GLU—GLY—

30
GLN—LEU—GLN—TRP—LEU—ASN—ARG—ARG—

40
ALA—ASN—ALA—LEU—LEU—ALA—ASN—GLY—

VAL—GLU—LEU—ARG—ASP—ASN—GLN—LEU—

50
VAL—VAL—PRO—SER—GLU—GLY—LEU—TYR—

60
LEU—ILE—TYR—SER—GLN—VAL—LEU—PHE—

70
LYS—GLY—GLN—GLY—CYS—PRO—SER—THR—

80
HIS—VAL—LEU—LEU—THR—HIS—THR—ILE—SER—

ARG—ILE—ALA—VAL—SER—TYR—GLN—THR—

90
LYS—VAL—ASN—LEU—LEU—SER—ALA—ILE—LYS—

100
SER—PRO—CYS—GLN—ARG—GLU—THR—PRO—

110
GLU—GLY—ALA—GLU—ALA—LYS—PRO—TRP—

120
TYR—GLU—PRO—ILE—TYR—LEU—GLY—GLY—

130
VAL—PHE—GLN—LEU—GLU—LYS—GLY—ASP—

ARG—LEU—SER—ALA—GLU—ILE—ASN—ARG—

140
PRO—ASP—TYR—LEU—ASP—PHE—ALA—GLU—

150
SER—GLY—GLN—VAL—TYR—PHE—GLY—ILE—

157
ILE—ALA—LEU.

5. A plasmid according to claim 1 wherein said structural gene for human TNF comprises the following DNA sequence (II):

(II)
GTCAGATCATCTTCTCGAACCCCGAGTGACAAGCCT
Val Arg Ser Ser Ser Arg Thr Pro Ser Asp Lys Pro
+1                                         10

GTAGCCCATGTTGTAGCAAACCCTCAAGCTGAGGGG
Val Ala His Val Val Ala Asn Pro Gln Ala Glu Gly
                              20

CAGCTCCAGTGGCTGAACCGCCGGGCCAATGCCCTC
Gln Leu Gln Trp Leu Asn Arg Arg Ala Asn Ala Leu
                           30

CTGGCCAATGGCGTGGAGCTGAGAGATAACCAGCTG
Leu Ala Asn Gly Val Glu Leu Arg Asp Asn Gln Leu
               40

GTGGTGCCATCAGAGGGCCTGTACCTCATCTACTCC
Val Val Pro Ser Glu Gly Leu Tyr Leu Ile Tyr Ser
       50                                 60

CAGGTCCTCTTGAAGGGCCAAGGCTGCCCCTCCACC
Gln Val Leu Phe Lys Gly Gln Gly Cys Pro Ser Thr
                              70

CATGTGCTCCTCACCCACACCATCAGCCGCATCGCC
His Val Leu Leu Thr His Thr Ile Ser Arg Ile Ala
                              80

GTCTCCTACCAGACCAAGGTCAACCTCCTCTCTGCC
Val Ser Tyr Gln Thr Lys Val Asn Leu Leu Ser Ala
                              90

ATCAAGAGCCCCTGCCAGAGGGAGACCCCAGAGGGG
Ile Lys Ser Pro Cys Gln Arg Glu Thr Pro Glu Gly
                           100

-continued
```
GCTGAGGCCAAGCCCTGGTATGACCCCATCTATCTC
Ala Glu Ala Lys Pro Trp Tyr Glu Pro Ile  Tyr Leu
   110                                        120

GGAGGGGTCTTCCAGCTGGAGAAGGGTGACCGACTC
Gly Gly Val Phe Gln Leu Glu Lys Gly Asp Arg Leu
                        130

AGCGCTGAGATCAATCGGCCCGACTATCTCGACTTT
Ser Ala Glu Ile Asn Arg Pro Asp Tyr Leu Asp Phe
                    140

GCCGAGTCTGGGCAGGTCTACTTTGGGATCATTGCC
Ala Glu Ser Gly Gln Val Tyr Phe Gly Ile Ile Ala
              150

CTG.
Leu
157
```

6. A process for producing human tumor necrosis factor (TNF) by extraction and purification from a culture of *E. coli*, said process comprising the steps of:
 a) transforming *E. coli* with a plasmid which comprises a structural gene for human TNF, a promoter element selected from the group consisting of the T4 phage promoter and a hybrid PL-T4 phage promoter, and a DNA fragment which comprises the trpA terminator, said promoter being operably linked to the hTNF structural gene, and said DNA fragment which comprises the trpA terminator being located at a point immediately downstream of said structural gene;
 b) culturing the transformed *E. coli* under conditions which optimize expression of TNF; and
 c) extracting and purifying said TNF therefrom.

7. A process according to claim 6 wherein said plasmid is of the ColE1 type and lacks a pBR322-derived rop gene, said gene having a function of controlling the replication of said plasmid.

8. A process according to claim 6 wherein a coding sequence for said terminator is contained in the following DNA fragment:

```
TCGACAGCCCGCCTAATGAGCGGGCTTTTTTTTCTCGG
   GTCGGGCGGATTACTCGCCCGAAAAAAAAGAGCCTTAA.
```

9. A process according to claim 6 wherein said TNF is a protein comprising the following amino acid sequence (I):

```
 1
VAL—ARG—SER—SER—SER—ARG—THR—PRO—

10
SER—ASP—LYS—PRO—VAL—ALA—HIS—VAL—

20
VAL—ALA—ASN—PRO—GLN—ALA—GLU—GLY—

30
GLN—LEU—GLN—TRP—LEU—ASN—ARG—ARG—

40
ALA—ASN—ALA—LEU—LEU—ALA—ASN—GLY—

VAL—GLU—LEU—ARG—ASP—ASN—GLN—LEU—

50
VAL—VAL—PRO—SER—GLU—GLY—LEU—TYR—

60
LEU—ILE—TYR—SER—GLN—VAL—LEU—PHE—

LYS—GLY—GLN—GLY—CYS—PRO—SER—THR—

80
HIS—VAL—LEU—LEU—THR—HIS—THR—ILE—SER—

ARG—ILE—ALA—VAL—SER—TYR—GLN—THR—

90
LYS—VAL—ASN—LEU—LEU—SER—ALA—ILE—LYS—

100
SER—PRO—CYS—GLN—ARG—GLU—THR—PRO—

110
GLU—GLY—ALA—GLU—ALA—LYS—PRO—TRP—

120
TYR—GLU—PRO—ILE—TYR—LEU—GLY—GLY—

130
VAL—PHE—GLN—LEU—GLU—LYS—GLY—ASP—

ARG—LEU—SER—ALA—GLU—ILE—ASN—ARG—

140
PRO—ASP—TYR—LEU—ASP—PHE—ALA—GLU—

150
SER—GLY—GLN—VAL—TYR—PHE—GLY—ILE—

157
ILE—ALA—LEU.
```
(I)

10. A process according to claim 6 wherein said structural gene for TNF comprises the following DNA sequence (II):

```
                                                    (II)
GTCAGATCATCTTCTCGAACCCCGAGTGACAAGCCT
Val Arg Ser Ser Ser Arg Thr Pro Ser Asp Lys Pro
+1                                      10

GTAGCCCATGTTGTAGCAAACCCTCAAGCTGAGGGG
Val Ala His Val Val Ala Asn Pro Gln Ala Glu Gly
                                        20

CAGCTCCAGTGGCTGAACCGCCGGGCCAATGCCCTC
Gln Leu Gln Trp Leu Asn Arg Arg Ala Asn Ala Leu
                          30

CTGGCCAATGGCGTGGAGCTGAGAGATAACCAGCTG
Leu Ala Asn Gly Val Glu Leu Arg Asp Asn Gln Leu
              40

GTGGTGCCATCAGAGGGCCTGTACCTCATCTACTCC
Val Val Pro Ser Glu Gly Leu Tyr Leu Ile Tyr Ser
   50                                   60

CAGGTCCTCTTGAAGGGCCAAGGCTGCCCCTCCACC
Gln Val Leu Phe Lys Gly Gln Gly Cys Pro Ser Thr
                               70

CATGTGCTCCTCACCCACACCATCAGCCGCATCGCC
His Val Leu Leu Thr His Thr Ile Ser Arg Ile Ala
                       80

GTCTCCTACCAGACCAAGGTCAACCTCCTCTCTGCC
Val Ser Tyr Gln Thr Lys Val Asn Leu Leu Ser Ala
                          90

ATCAAGAGCCCCTGCCAGAGGGAGACCCCAGAGGGG
Ile Lys Ser Pro Cys Gln Arg Glu Thr Pro Glu Gly
                          100
```

```
GCTGAGGCCAAGCCCTGGTATGACCCCATCTATCTC
Ala Glu Ala Lys Pro Trp Tyr Glu Pro Ile Tyr Leu
110                                          120

GGAGGGGTCTTCCAGCTGGAGAAGGGTGACCGACTC
Gly Gly Val Phe Gln Leu Glu Lys Gly Asp Arg Leu
                    130
```

-continued
```
AGCGCTGAGATCAATCGGCCCGACTATCTCGACTTT
Ser Ala Glu Ile Asn Arg Pro Asp Tyr Leu Asp Phe
                            140

GCCGAGTCTGGGCAGGTCTACTTTGGGATCATTGCC
Ala Glu Ser Gly Gln Val Tyr Phe Gly Ile Ile Ala
                        150

CTG.
Leu
157
```

* * * * *

UNITED STATES PATENT AND TRADEMARK OFFICE
CERTIFICATE OF CORRECTION

PATENT NO. : 5,059,530
DATED : October 22, 1991
INVENTOR(S) : OSHIMA et al.

It is certified that error appears in the above-identified patent and that said Letters Patent is hereby corrected as shown below:

On the title page:

Item [63], change 6,907,816 to 907,816

Signed and Sealed this

Eighteenth Day of May, 1993

Attest:

MICHAEL K. KIRK

Attesting Officer

Acting Commissioner of Patents and Trademarks